United States Patent
Kwok et al.

(10) Patent No.: US 10,058,666 B2
(45) Date of Patent: *Aug. 28, 2018

(54) CPAP SYSTEMS

(71) Applicant: RESMED LIMITED, Bella Vista, New South Wales (AU)

(72) Inventors: Philip Rodney Kwok, Sydney (AU); Bruce Gregory, Sydney (AU); Karthikeyan Selvarajan, Sydney (AU); James Morrison, Sydney (AU)

(73) Assignee: RESMED LIMITED, Bella Vista, New South Wales (AU)

( * ) Notice: Subject to any disclaimer, the term of this patent is extended or adjusted under 35 U.S.C. 154(b) by 278 days.

This patent is subject to a terminal disclaimer.

(21) Appl. No.: 14/878,044

(22) Filed: Oct. 8, 2015

(65) Prior Publication Data

US 2016/0022935 A1 Jan. 28, 2016

Related U.S. Application Data

(60) Continuation of application No. 13/658,247, filed on Oct. 23, 2012, now Pat. No. 9,182,062, which is a
(Continued)

(51) Int. Cl.
*A61M 16/08* (2006.01)
*A61M 16/00* (2006.01)
*F16L 31/00* (2006.01)

(52) U.S. Cl.
CPC .... *A61M 16/0057* (2013.01); *A61M 16/0003* (2014.02); *A61M 16/08* (2013.01);
(Continued)

(58) Field of Classification Search
CPC .............. A61M 16/00; A61M 16/0003; A61M 16/0051; A61M 16/0057; A61M 16/0063;
(Continued)

(56) References Cited

U.S. PATENT DOCUMENTS 3,754,551 A  8/1973 Nielsen
4,257,415 A  3/1981 Rubin
(Continued)

FOREIGN PATENT DOCUMENTS

DE  4020522  1/1992
EP  1516641  3/2005
(Continued)

OTHER PUBLICATIONS

Kwok, U.S. Appl. No. 60/656,880, filed Mar. 1, 2005.
(Continued)

*Primary Examiner* — Annette Dixon
(74) *Attorney, Agent, or Firm* — Nixon & Vanderhye P.C.

(57) ABSTRACT

A CPAP system includes a flow generator, a patient interface, an air delivery conduit that interconnects the flow generator and the patient interface, and a packaging arrangement including at least one storage facilitating member to allow storage of the air delivery conduit. The at least one storage facilitating member may be provided to the flow generator, a cradle, and/or the air delivery conduit.

19 Claims, 15 Drawing Sheets

Related U.S. Application Data division of application No. 11/988,809, filed as application No. PCT/AU2006/001169 on Aug. 15, 2006, now Pat. No. 8,316,848.

(60) Provisional application No. 60/707,950, filed on Aug. 15, 2005.

(52) U.S. Cl.
CPC ......... A61M 16/0875 (2013.01); F16L 31/00 (2013.01); A61M 2205/3334 (2013.01)

(58) Field of Classification Search
CPC .......... A61M 16/0066; A61M 16/0069; A61M 16/01; A61M 16/08; A61M 16/0833; A61M 16/0875; A61M 16/1045; A61M 16/107; A61M 16/16; A61M 16/22; A61M 2016/0027; A61M 2016/0036; A61M 2205/3334; A61M 2205/3358; A61M 2205/3569; A61M 2205/3592; A61M 2205/52; A61M 2205/6018; A61M 2205/6054; A61M 2230/10; A61M 2230/18; A61M 2230/432; A61M 2230/60; A61M 2230/63; A62B 18/006; A62B 31/00; A62B 7/10; A63B 2208/053; A63B 2208/056; A61B 5/0066; A61B 5/0068; A61B 5/0084; A61B 5/6852; A61B 5/6853; A47G 9/0215; A61F 2007/006; A61F 7/0097; A61G 10/023; A61G 10/026
USPC ............ 128/200.24, 201.23, 202.12, 202.22, 128/204.18, 204.21, 204.22, 204.24, 128/205.12, 205.23, 205.26, 205.28, 128/206.12, 206.17

See application file for complete search history.

(56) References Cited

U.S. PATENT DOCUMENTS

| | | | | |
|---|---|---|---|---|
| 4,695,955 | A | 9/1987 | Faisandier | |
| 4,768,496 | A | 9/1988 | Kreizman et al. | |
| 4,776,990 | A | 10/1988 | Verity | |
| 4,944,310 | A | 7/1990 | Sullivan | |
| 4,949,715 | A | 8/1990 | Brugger | |
| 5,007,666 | A | 4/1991 | Kyfes | |
| 5,109,837 | A * | 5/1992 | Gamow | A61G 10/026 128/200.24 |
| 5,117,819 | A | 6/1992 | Servidio et al. | |
| 5,127,400 | A | 7/1992 | DeVries et al. | |
| 5,159,641 | A | 10/1992 | Sopko et al. | |
| 5,345,929 | A | 9/1994 | Jansson et al. | |
| 5,413,097 | A * | 5/1995 | Birenheide | A62B 7/10 128/202.22 |
| 5,809,997 | A | 9/1998 | Wolf | |
| 5,813,404 | A | 9/1998 | Devlin et al. | |
| 5,950,621 | A | 9/1999 | Klockseth et al. | |
| 6,035,851 | A | 3/2000 | Wallen | |
| 6,142,949 | A | 11/2000 | Ubby | |
| 6,148,815 | A | 11/2000 | Wolf | |
| 6,286,876 | B1 | 9/2001 | Jasperse et al. | |
| 6,321,764 | B1 | 11/2001 | Gauger et al. | |
| 6,333,695 | B2 | 12/2001 | Young | |
| 6,349,724 | B1 * | 2/2002 | Burton | A61M 16/0057 128/204.18 |
| 6,910,483 | B2 | 6/2005 | Daly et al. | |
| 7,121,276 | B2 | 10/2006 | Jagger et al. | |
| 7,148,806 | B2 * | 12/2006 | Anttila | A61M 16/22 128/205.12 |
| 7,151,456 | B2 | 12/2006 | Godfrey | |
| 7,159,587 | B2 | 1/2007 | Drew et al. | |
| 7,191,777 | B2 | 3/2007 | Brand et al. | |
| 7,350,520 | B2 | 4/2008 | Richard-Bey | |
| 7,469,698 | B1 | 12/2008 | Childers et al. | |
| 7,520,277 | B1 * | 4/2009 | Grady | A61G 10/023 128/201.23 |
| 7,762,289 | B2 | 7/2010 | McCulloh et al. | |
| 7,913,689 | B2 | 3/2011 | Henry et al. | |
| 8,316,848 | B2 * | 11/2012 | Kwok | A61M 16/0057 128/204.18 |
| 2002/0058974 | A1 * | 5/2002 | Van Duren | A47G 9/0215 607/96 |
| 2002/0174867 | A1 | 11/2002 | Gunaratnam | |
| 2002/0198458 | A1 * | 12/2002 | Tripp, Jr. | A61B 5/0066 600/476 |
| 2003/0154981 | A1 | 8/2003 | Spruiell | |
| 2003/0196662 | A1 | 10/2003 | Ging et al. | |
| 2004/0182386 | A1 | 9/2004 | Meier | |
| 2004/0210151 | A1 | 10/2004 | Tsukashima et al. | |
| 2004/0226566 | A1 | 11/2004 | Gunaratnam et al. | |
| 2005/0039747 | A1 | 2/2005 | Fukunaga et al. | |
| 2006/0157057 | A1 | 7/2006 | Palmquist | |
| 2007/0144519 | A1 | 6/2007 | Henry et al. | |
| 2010/0147301 | A1 | 6/2010 | Kwok | |
| 2010/0236552 | A1 | 11/2010 | Kwok et al. | |
| 2011/0139154 | A1 | 6/2011 | Henry et al. | |
| 2013/0042867 | A1 | 2/2013 | Kwok et al. | |

FOREIGN PATENT DOCUMENTS

| | | |
|---|---|---|
| EP | 1579884 | 9/2005 |
| GB | 2047868 | 12/1980 |
| WO | 2004/060443 | 7/2004 |
| WO | 2005/002655 | 2/2005 |
| WO | 2006/125252 | 11/2006 |

OTHER PUBLICATIONS

European Search Report issued in Application No. 06126895, dated Jun. 13, 2007.
International Search Report issued in Application No. PCT/AU2006/001169, dated Nov. 29, 2006.
International Search Report issued in Application No. PCT/AU2006/001169, dated Feb. 20, 2008.
Written Opinion issued in Application No. PCT/AU2006/001169, dated Nov. 29, 2006.

* cited by examiner

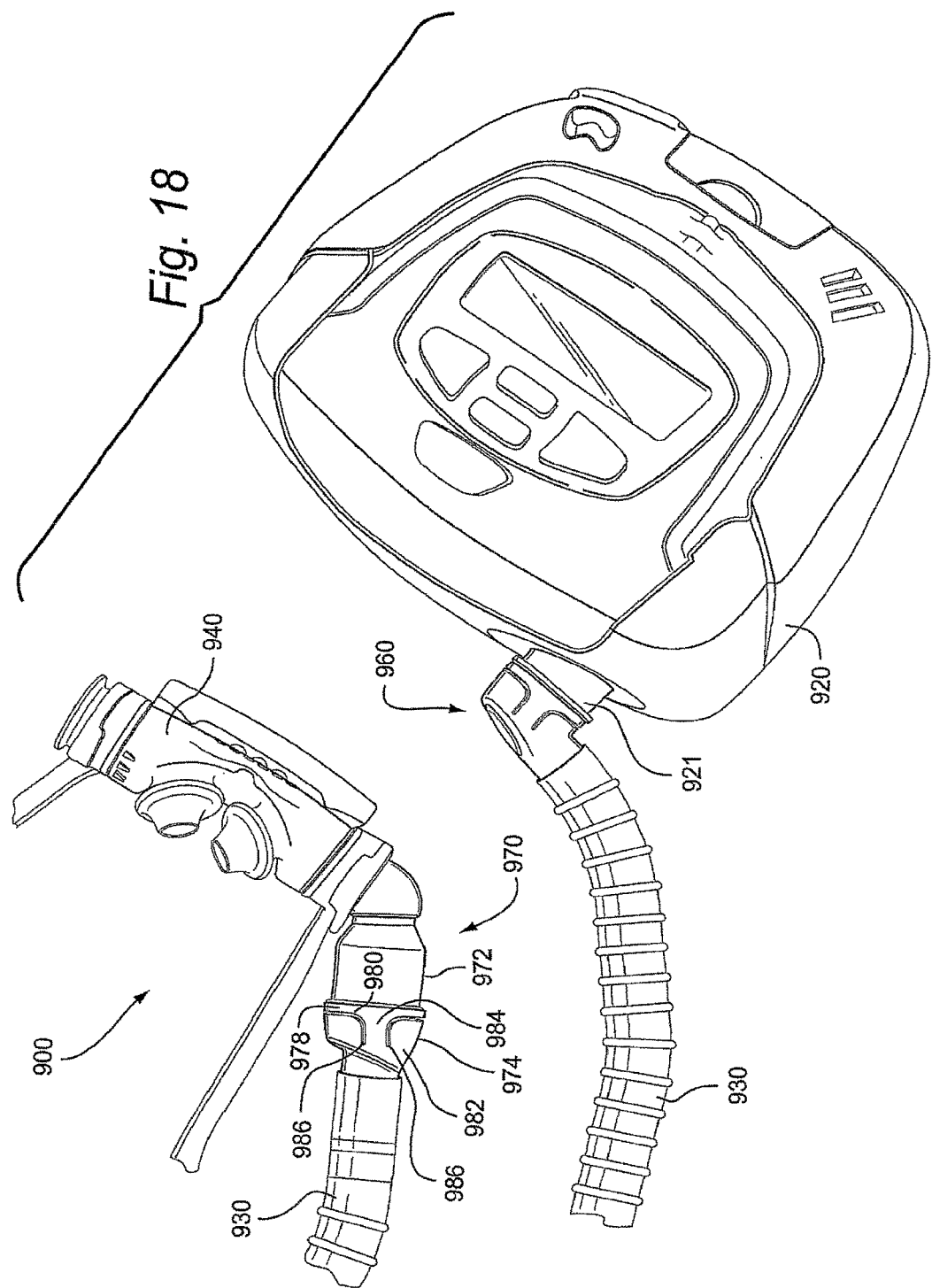

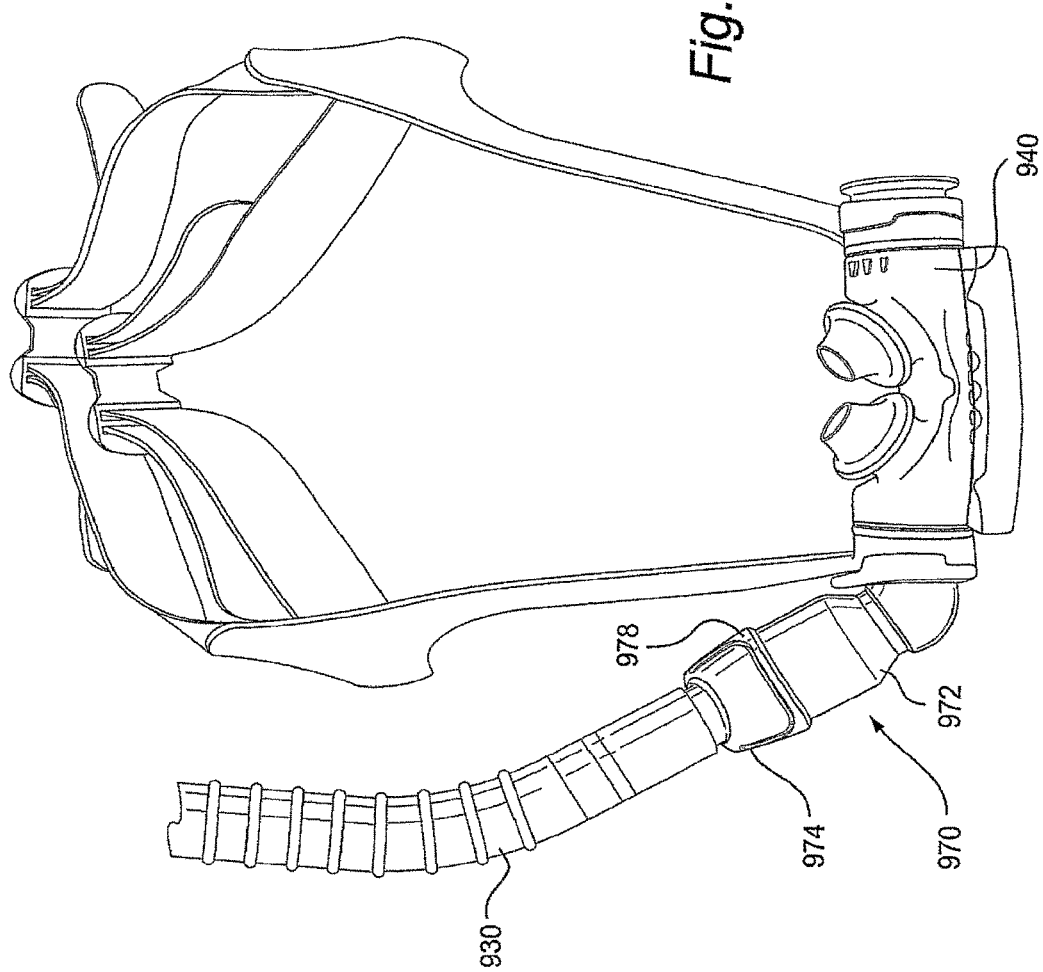

CPAP SYSTEMS

CROSS-REFERENCE TO RELATED APPLICATIONS

This application is a continuation of application Ser. No. 13/658,247, filed Oct. 23, 2012 (now U.S. Pat. No. 9,182,062), which is a divisional of application Ser. No. 11/988,809, filed Jan. 15, 2008 (now U.S. Pat. No. 8,316,848), which is the U.S. National Phase of International Application No. PCT/AU2006/001169, filed Aug. 15, 2006, which claims the benefit of U.S. Provisional Application No. 60/707,950, filed Aug. 15, 2005, the entire contents of each of which is incorporated herein by reference in its entirety.

FIELD OF THE INVENTION

The present invention relates to a CPAP system that delivers breathable gas to a patient.

BACKGROUND OF THE INVENTION

Colin Sullivan was the first to invent the use of nasal Continuous Positive Airway Pressure (CPAP) to treat Obstructive Sleep Apnea (OSA), e.g., see U.S. Pat. No. 4,944,310. The treatment generally provides a supply of air or breathable gas from a blower to a patient via an air delivery conduit and a patient interface, such as a full-face or nasal mask or nasal prongs. The air or breathable gas is commonly delivered at a pressure of 4 $cmH_2O$ to 20 $cmH_2O$ and acts as a splint to hold the airway open during sleep.

Patient compliance and acceptance of CPAP therapy is a major driver of the industry. To address this issue, emphasis has been placed on reducing the size of CPAP systems to enhance the look and feel of the systems for patients. There are three major components in a CPAP system, i.e., a flow generator, an air delivery conduit, and a patient interface. To date, there has been a focus on reducing the size of the flow generator and developing less intrusive patient interfaces. However, there has been very little attention paid to the size of the air delivery conduit, which acts as the interface between the patient interface and the flow generator. For example, there is a Kaerys KXS CPAP machine that is supplied with 15 mm tubing. However, the tubing may only be used for pressures up to 15 $cmH_2O$. In order to effectively increase compliance, all components of a CPAP system should be reduced in size and allow a broad range of pressures to be delivered. A smaller CPAP system also provides for smaller packaging requirements.

The air delivery conduit typically used in CPAP therapy has been medical grade tubing as found in hospitals with a diameter of 22 mm. As CPAP therapy is generally conducted in the home, this medical tubing can make users apprehensive in adopting the therapy because the medical tubing can look out of place amongst the environment commonly found in a user's bedroom. In addition, the tubing may be bulky and not easily packed up or organized to preserve the look of a bedroom. Furthermore, the sound caused by the medical tubing as it brushes against linen and the added physical interference as far as drag to the patient interface can cause the user some discomfort. There is no current standard ISO tubing size other than 22 mm available for use with CPAP systems across the full flow generator pressure range.

Also, current tubing can communicate airflow but are restrictive in communicating electrical signals. Currently, only external insulation, e.g., in the form of a sock or sheath over the tubing, has been added as an accessory to the tubing to reduce "rain out", which is the collection of water caused from the humidifier within the tubing.

The problems with using tubing with a smaller bore include the high impedance in the tube to provide the desired pressure at the patient interface. Presently, flow generators are not able to supply sufficient power for the full pressure range required. Also, there are large pressure swings due to the flow generator not being able to respond quickly enough to changes in pressure. Thus, a need has emerged in the art to address these problems.

SUMMARY OF THE INVENTION

One aspect of the invention relates to an air delivery conduit for a CPAP system that is smaller in size and provides an easy and quick connection between the patient interface and flow generator. This arrangement will allow the entire CPAP system to be smaller and packaged more compactly.

Another aspect of the invention relates to a CPAP system that provides a more comfortable look and feel for the patient.

Another aspect of the invention relates to a CPAP system that is structured to facilitate storage (e.g., wrapping) of the air delivery conduit.

Another aspect of the invention relates to a CPAP system including a flow generator, a patient interface, an air delivery conduit that interconnects the flow generator and the patient interface, and a packaging arrangement including at least one storage facilitating member to allow storage of the air delivery conduit. The at least one storage facilitating member may be provided to the flow generator, a cradle, and/or the air delivery conduit.

Another aspect of the invention relates to a CPAP system including a flow generator including a blower that supplies breathable gas at a pressure of 3-20 $cmH_2O$ (e.g., a full range of therapy pressures appropriate for CPAP), a patient interface, and an air delivery conduit interconnecting the flow generator and the patient interface. The air delivery conduit includes a conduit portion having a diameter less than 22 mm.

Yet another aspect of the invention relates to a CPAP system including a flow generator providing an outlet, an air delivery conduit, a flow generator connector that couples one end of the air delivery conduit to the outlet of the flow generator, and a recognition system structured to recognize or identify a type of air delivery conduit that is connected to the CPAP system.

Still another aspect of the invention relates to a CPAP system including a flow generator providing an outlet, a patient interface, an air delivery conduit, and a snap-fit flow generator connector provided between one end of the air delivery conduit and the outlet.

Still another aspect of the invention relates to a low friction air delivery conduit for use with an apparatus that delivers a supply of pressurized breathable air to a patient. The low friction air delivery conduit including a tubular wall having an internal diameter and one or more support webs that internally support the tubular wall. The one or more webs are arranged to extend across the internal diameter or a part thereof or a chord of the tubular wall. The tubular wall is structured such that at least an external surface is relatively smooth to provide relatively low friction properties.

Other aspects, features, and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of this invention. In such drawings:

FIG. 18 is a perspective view of a CPAP system according to yet another embodiment of the invention;

FIG. 19 is an isolated perspective view of a patient interface of the CPAP system shown in FIG. 18;

DETAILED DESCRIPTION OF ILLUSTRATED EMBODIMENTS

1. CPAP System

A CPAP system generally includes a flow generator, an air delivery conduit, and a patient interface. In use, the flow generator generates a supply of pressurized air that is delivered to the patient via an air delivery conduit that includes one end coupled to the outlet of the flow generator and an opposite end coupled to the patient interface. The patient interface comfortably engages the patient's face and provides a seal. The patient interface may have any suitable configuration as is known in the art, e.g., full-face mask, nasal mask, oro-nasal mask, mouth mask, nasal prongs, etc. Also, any suitable headgear arrangement may be utilized to comfortably support the patient interface in a desired position on the patient's face.

2. CPAP System Packaging Arrangement

FIGS. 1-11C illustrate compact CPAP systems according to embodiments of the present invention. The compact CPAP systems are structured to facilitate the transport and/or convenient storage of the systems. These compact CPAP systems may be especially beneficial for CPAP users who wish to travel with their CPAP systems.

2.1 CPAP Systems that Allow Wrapping of the Air Delivery Conduit

FIGS. 1-8C illustrate CPAP systems that allow the air delivery conduit to be stored (e.g., wrapped or packaged) around the flow generator to provide an orderly, compact System.

2.1.1 Cradle for Flow Generator

Figure 1:
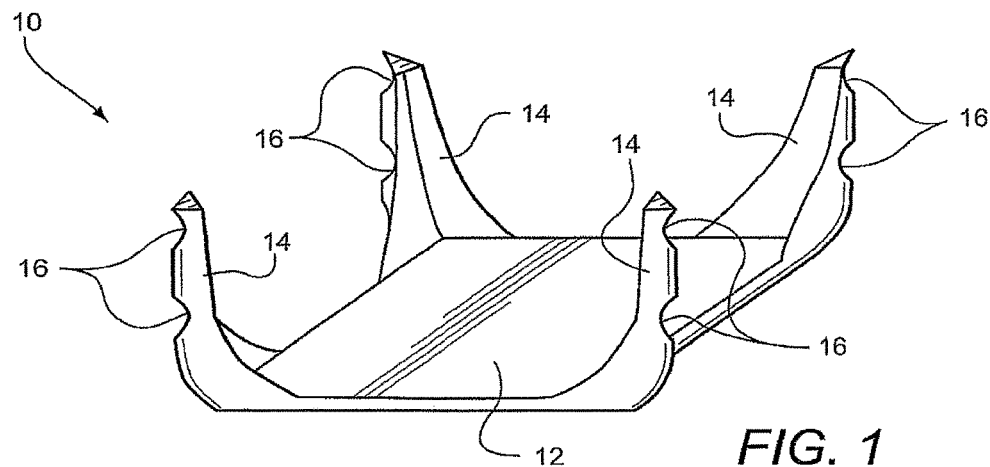
FIG. 1 is a perspective view of a cradle for a CPAP system according to an embodiment of the invention, the cradle allowing storage of an air delivery conduit.

FIG. 1 illustrates a cradle 10 that is adapted to support a flow generator of a CPAP system. Specifically, the cradle 10 includes a base 12 for supporting the flow generator thereon and a hose supporting or storage facilitating member or device, e.g., one or more upwardly extending arms 14, e.g., four upwardly extending arms 14 positioned on the cradle, e.g., at or near respective corners of the base 12. In an embodiment, the arms 14 are adapted to releasably engage, e.g., clip onto, the flow generator to attach the cradle 10 to the flow generator. In use, the air delivery conduit may be wrapped around the arms 14 for storage purposes. In the illustrated embodiment, each of the arms 14 includes one or more grooves 16 for receiving the air delivery conduit as it is wrapped therearound.

2.1.2 Flow Generator with Rings

Figure 2A:
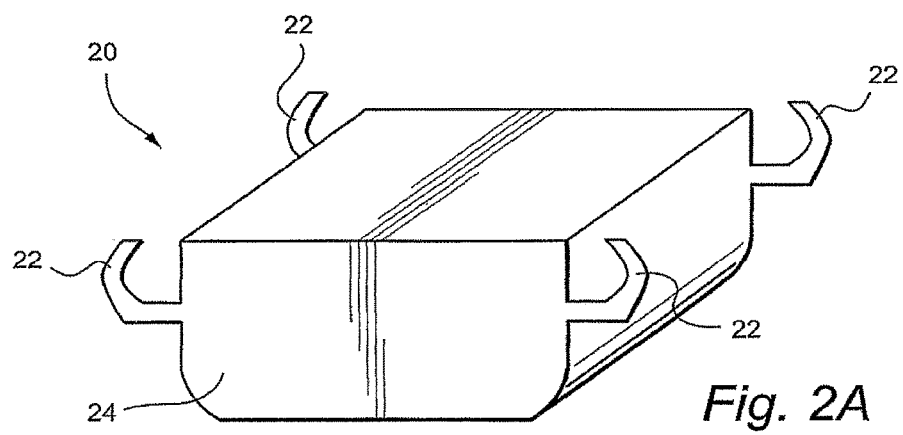
FIG. 2A is a perspective view of a flow generator for a CPAP system according to another embodiment of the invention, the flow generator including an outer body having rings to allow wrapping of an air delivery conduit.

FIG. 2A illustrates a flow generator 20 for a CPAP system that includes a hose supporting or storage facilitating member or device in the form of one or more rings or hooks 22, e.g., four rings 22 positioned on the flow generator, e.g., at or near respective corners of the flow generator 20. The rings or hooks 22 may be formed separately from the outer body 24 of the flow generator 20 and attached thereto. Alternatively, the rings or hooks 22 may be molded in one piece along with the outer body 24 of the flow generator 20. In use, the air delivery conduit may be wrapped around the rings or hooks 22 for storage purposes.

Figure 2B:
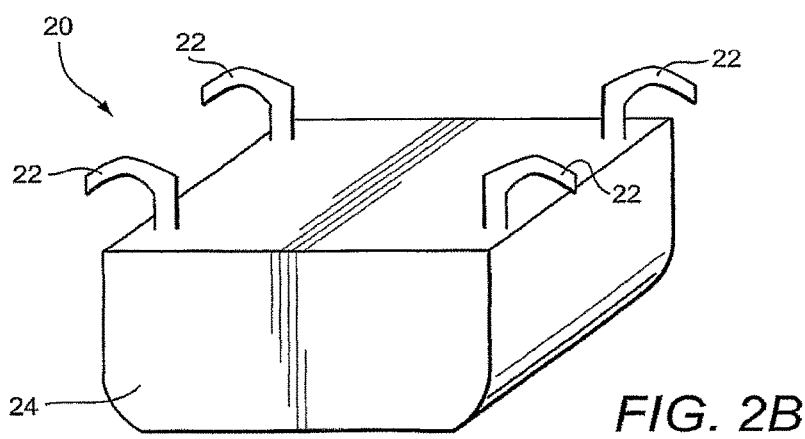
FIG. 2B is an alternative embodiment of the flow generator shown in FIG. 2A.

In the illustrated embodiment of FIG. 2A, the rings or hooks 22 extend from respective sides of the outer body 24 and the free end of each ring or hook 22 is directed generally upwardly and inwardly with respect to a side of the outer body 24. However, the rings or hooks 22 may have other suitable configurations. For example, as shown in FIG. 2B, the rings or hooks 22 may extend from a top of the outer body 24 and the free end of each ring or hook 22 may be directed generally upwardly and outwardly with respect to a side of the outer body 24.

2.1.3 Flow Generator with Slats

Figure 3A:
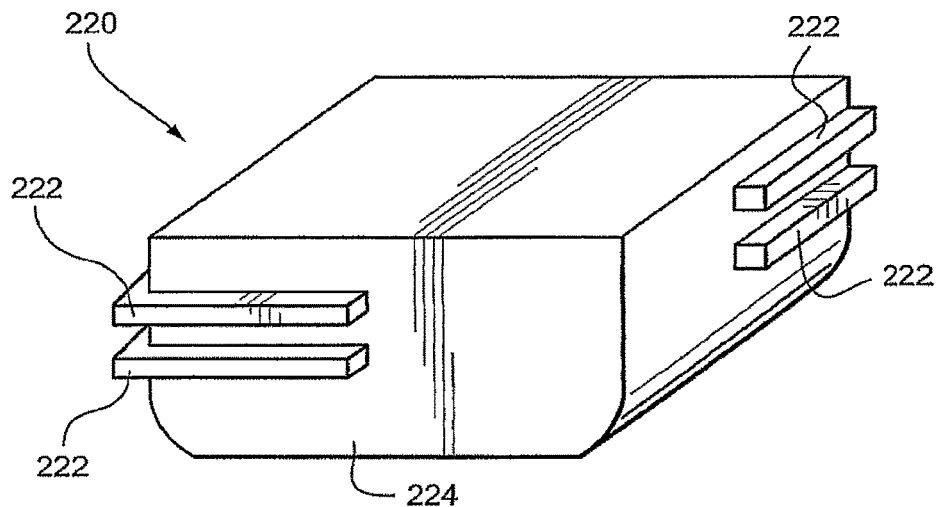
FIG. 3A is a perspective view of a flow generator for a CPAP system according to another embodiment of the invention, the flow generator including an outer body having slats to allow wrapping of an air delivery conduit.

FIG. 3A illustrates a flow generator 220 for a CPAP system that includes a hose supporting or storage facilitating member or device in the form of one or more slats 222 (or elongated protrusions or strips), e.g., spaced apart slats 222 positioned on the flow generator, e.g., at or near opposing corners of the flow generator 220. The slats 222 may be formed separately from the outer body 224 of the flow generator 220 and attached thereto. Alternatively, the slats 222 may be molded in one piece along with the outer body 224 of the flow generator 220. In use, the air delivery conduit may be wrapped around the flow generator 220 and retained between the slats 222 for storage purposes.

Figure 3B:
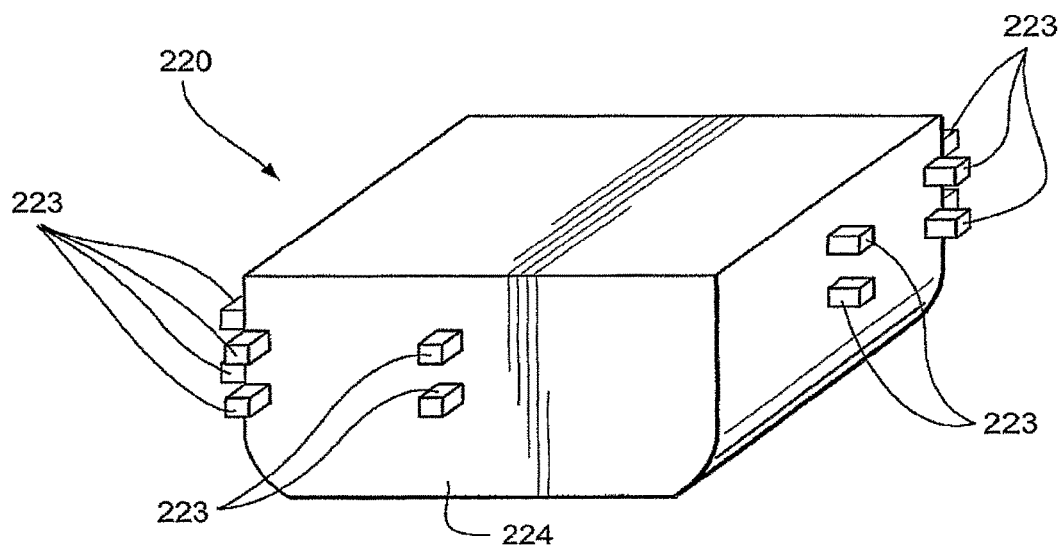
FIG. 3B is an alternative embodiment of the flow generator shown in FIG. 3A.

In an alternative embodiment, as shown in FIG. 3B, the flow generator 220 may include an array of little pegs 223 (rather than continuous slats 222). As illustrated, the pegs 223 protrude from sides of the body 224 (e.g., at or near opposing corners of the flow generator) and cooperate to provide a channel for the air delivery conduit to wrap around the flow generator.

2.1.4 Flow Generator with External Ribs

Figure 4A:
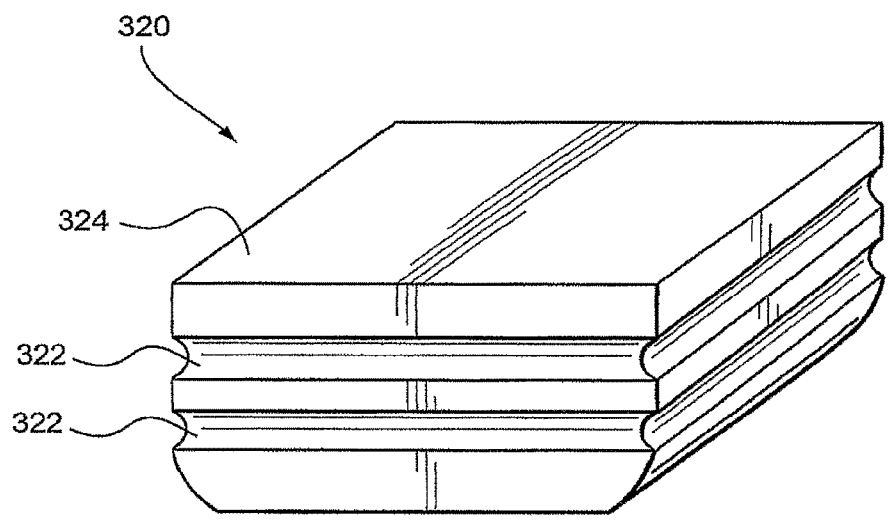
FIG. 4A is a perspective view of a flow generator for a CPAP system according to another embodiment of the invention, the flow generator including an outer body having a ribbed outer surface to allow wrapping of an air delivery conduit.

FIG. 4A illustrates a flow generator 320 for a CPAP system that includes a hose supporting or storage facilitating member or device in the form of one or more ribs 322 (or grooves) that provide ribbed outer surfaces, e.g., two external ribs 322 that extend around the periphery of the flow generator 320. In an embodiment, the ribs 322 may be molded in one piece along with the outer body 324 of the flow generator 320. In use, the air delivery conduit may be wrapped around the flow generator 320 and retained within the ribs 322 for storage purposes.

Figure 4B:
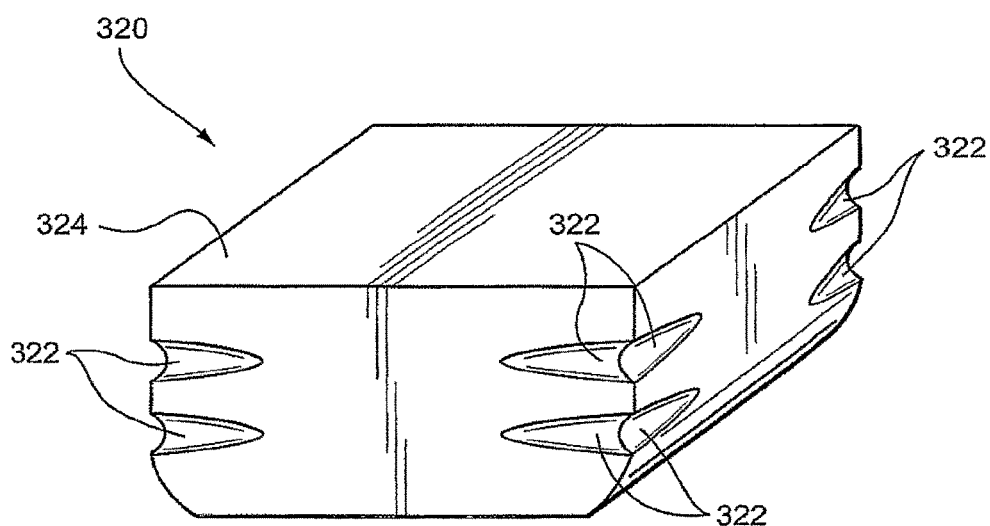
FIG. 4B is an alternative embodiment of the flow generator shown in FIG. 4A.

In an alternative embodiment, as shown in FIG. 4B, ribs 322 may only be provided on corners of the flow generator 320. As illustrated, the ribs 322 taper out or away from the respective corner.

2.1.5 Flow Generator with Handle

Figure 5:
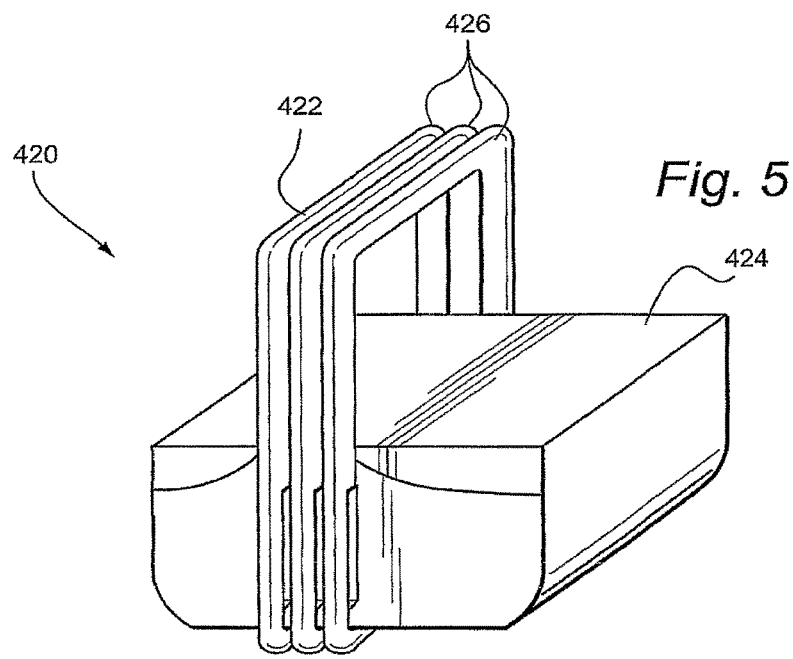
FIG. 5 is a perspective view of a flow generator for a CPAP system according to another embodiment of the invention, the flow generator including an outer body having a handle adapted to allow wrapping of an delivery conduit.

FIG. 5 illustrates a flow generator 420 for a CPAP system that includes a hose supporting or storage facilitating member or device in the form of a handle 422, e.g., handle 422 that extends above the flow generator 420 for carrying purposes. The handle 422 may be formed separately from the outer body 424 of the flow generator 420 and attached thereto. Alternatively, the handle 422 may be molded in one piece along with the outer body 424 of the flow generator 420. In use, the air delivery conduit may be wrapped around the handle 422 for storage purposes. In the illustrated embodiment, the handle 422 may include a plurality of tube-like portions 426, e.g., three tube-like portions 426, that provide grooves therebetween for retaining the air delivery conduit.

Figure 6:
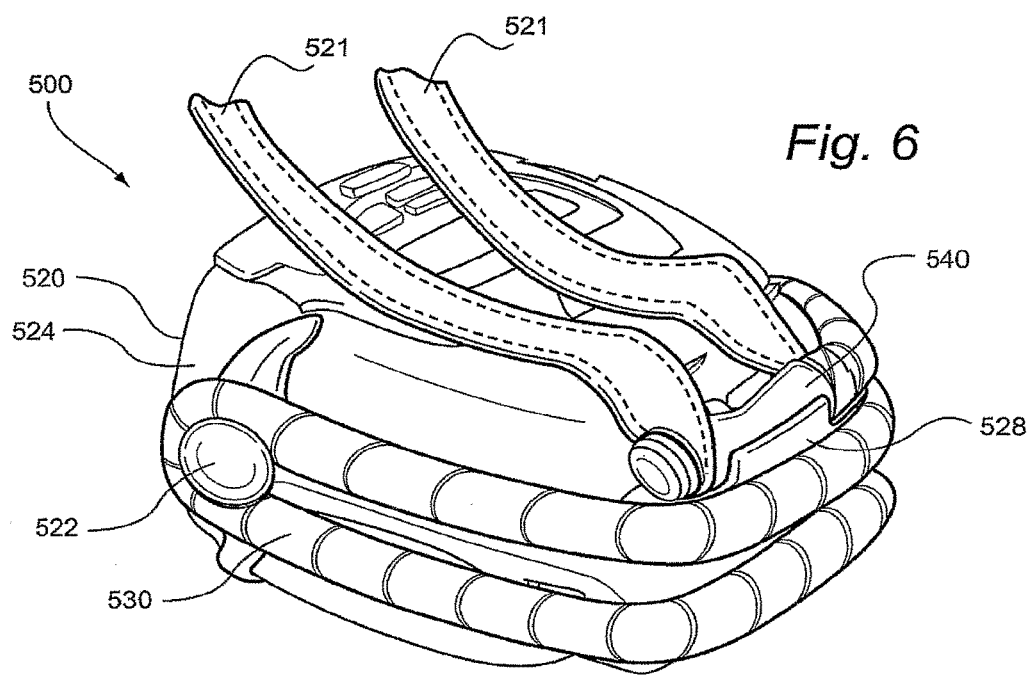
FIG. 6 is a perspective view of a CPAP system according to another embodiment of the invention, the CPAP system including a flow generator that allows wrapping of an air delivery conduit and support of a patient interface.

2.1.6 Flow Generator with Conduit Retaining Members and Patient Interface Support FIG. 6 illustrates a compact CPAP system 500 including a flow generator 520, an air delivery conduit 530, and a patient interface 540, e.g., nasal assembly with headgear straps 521 (partially illustrated). As illustrated, the flow generator 520 includes conduit retaining members 522, e.g., posts, on opposing sides of the flow generator 520 that allows the air delivery conduit 530 to be wrapped around the flow generator 520 for storage purposes. Also, the flow generator 520 may include a patient interface support 528, e.g., cradle, that supports and retains the patient interface 540 on the flow generator 520 for storage purposes. In this embodiment, the support 528 is structured to support a SWIFT® mask as described in published as U.S. Patent Publication No. 2004-0226566, incorporated herein by reference, although other patient interface supports can be configured to support patient interfaces having other styles and/or shapes. The retaining members 522 and/or patient interface support 528 may be formed separately from the outer body 524 of the flow generator 520 and attached thereto. Alternatively, the retaining members 522 and/or patient interface support 528 may be molded in one piece along with the outer body 524 of the flow generator 520.

2.1.7 Stand for Flow Generator/Cradle

Figure 7:
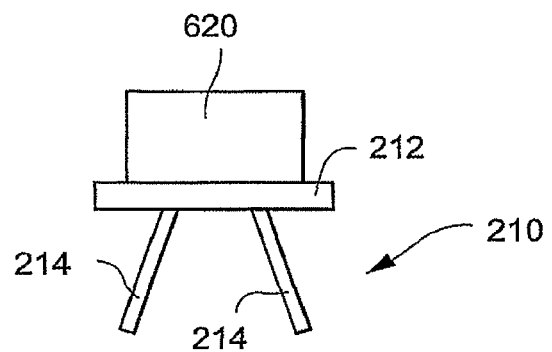
FIG. 7 is a schematic view of stand for a flow generator according to another embodiment of the invention.

FIG. 7 illustrates a stand 210 that is adapted to support a flow generator 620 of a CPAP system. Specifically, the stand 210 includes a top support 212 for supporting the flow generator 620 thereon and two or more legs 214 provided, e.g., removably attached, to the top support 212 to elevate the top support 212 from the ground. The top support 212 and/or flow generator 620 may include one or more orienting structures, e.g., slots/protrusions, to orient and/or secure the flow generator 620 to the top support 212. The legs 214 may be in the form of a hose supporting or storage facilitating member or device Structured to allow the air delivery conduit to be wrapped therearound for storage purposes. In an embodiment, the stand 210 may be adapted to support a flow generator cradle, such as the cradle 10 shown in FIG. 1.

2.1.8 Legs Provided to Flow Generator/Cradle

Figure 8A:
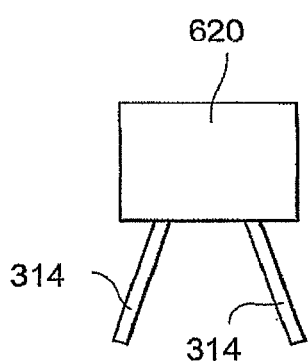
FIGS. 8A-8C are schematic views of attachable legs for a flow generator according to another embodiment of the invention.
Figure 8B:
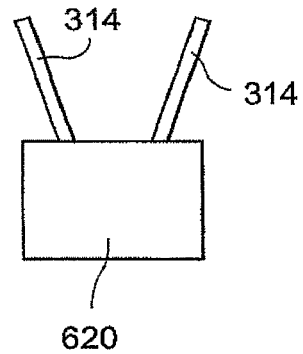
Figure 8C:
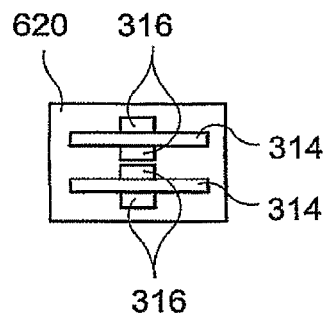

FIGS. 8A-8B illustrate a flow generator 620 including one or more legs 314 provided, e.g., removably attached, thereto. In use, the air delivery conduit may be wrapped around the legs 314 for storage purposes. As shown in FIG. 8A, the legs 314 may be provided to the flow generator 620 to elevate the flow generator 620 from the ground. Alternatively, as shown in FIG. 8B, the legs 314 may be provided to the flow generator 620 so they extend upwardly from the flow generator 620. In an embodiment, the legs 314 may be removably attached to the flow generator 620 so that the legs 314 may be detached and stored on the flow generator 620, e.g., by clips 316, when the air delivery conduit is in use as shown in FIG. 8C.

2.2 Compact Air Delivery Conduits

FIGS. 9-11C illustrate compact air delivery conduits that are structured to reduce the size or bulkiness of the CPAP system, thereby enhancing the packaging of the CPAP system.

2.2.1 Telescopic Air Delivery Conduit

Figure 9:
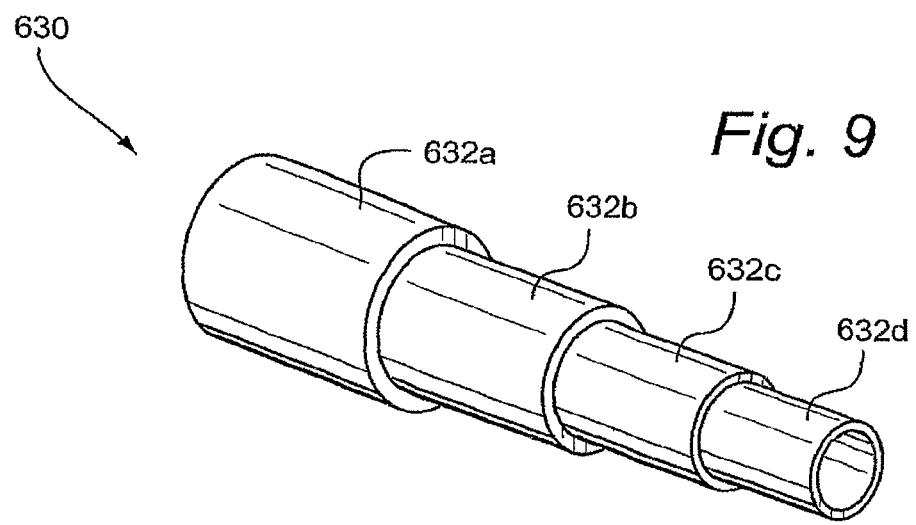
FIG. 9 is a perspective view of a telescoping air delivery conduit according to another embodiment of the invention.

FIG. 9 illustrates an air delivery conduit 630 for a CPAP system that has a telescopic configuration. Specifically, the air delivery conduit 630 includes a plurality of conduit portions, e.g., four conduit portions 632*a*, 632*b*, 632*c*, and 632*d*, that are mounted in telescoping relation. In use, the conduit portions 632*a*, 632*b*, 632*c*, and 632*d* are extended and cooperate to provide an elongated air flow passage as shown in FIG. 9. When the air delivery conduit 630 is not in use, the conduit portions 632a, 632b, 632c, and 632d may be retracted in telescoping relation for compact storage, such that the size of the air delivery conduit 630 is greatly reduced, e.g., to the size of a single conduit portion 632a. This arrangement also allows the retracted air delivery conduit 630 to be placed within a storage Compartment, e.g., provided by the flow generator, so that the air delivery conduit 630 may be completely packaged away.

2.2.2 Collapsible Air Delivery Conduit

Figure 10A:
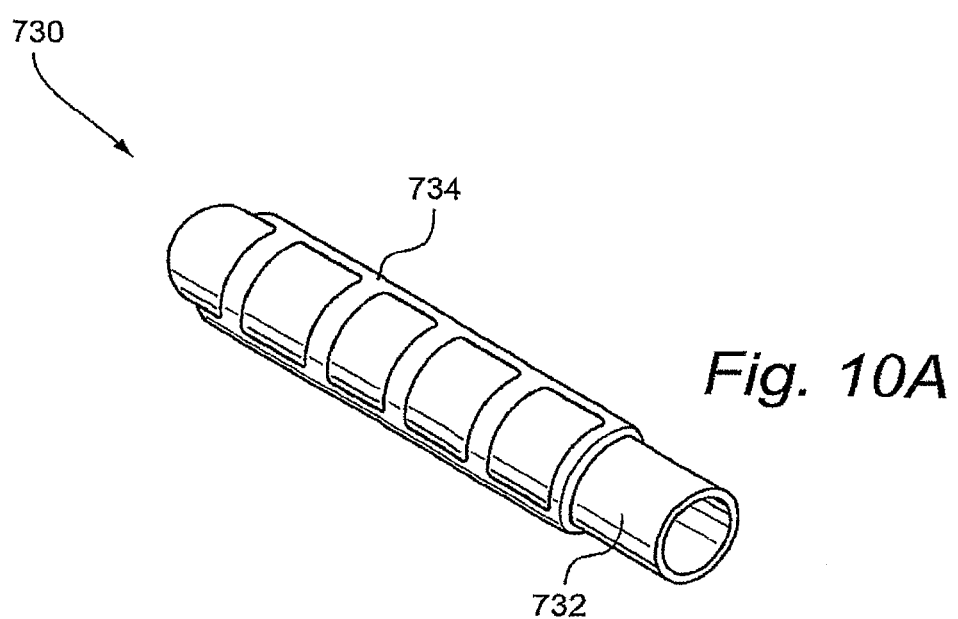
FIG. 10A is a perspective view of an air delivery conduit according to another embodiment of the invention, the air delivery conduit filled with pressurized air.
Figure 10B:
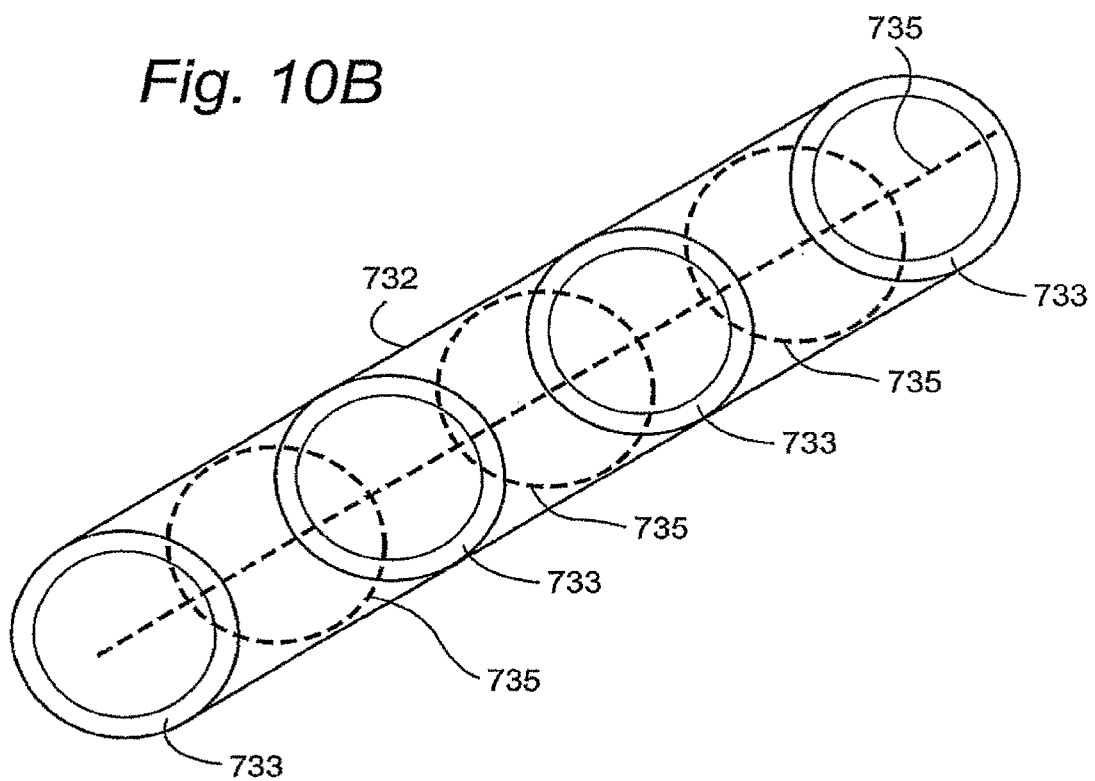
FIG. 10B illustrates an air delivery conduit according to an embodiment of the present invention that includes built-in solid hoops.
Figure 10C:
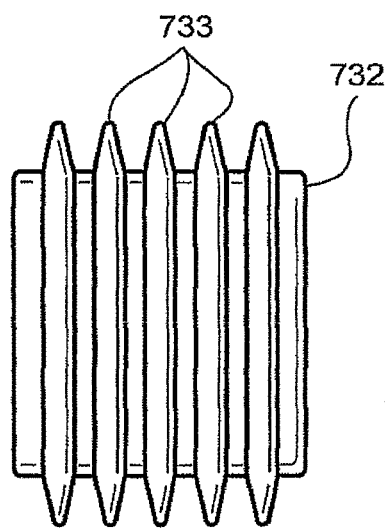
FIG. 10C illustrates the air delivery conduit shown in FIG. 10B in a compressed storage condition.

FIG. 10A illustrates an air delivery conduit 730 for a CPAP system that may be collapsible to a substantially flat condition in order to facilitate storage in a compact manner. In use, the air delivery conduit 730 will automatically expand to the required diameter due to the introduction of pressurized air to provide a substantially rigid tube for allowing the passage of air therethrough as shown in FIG. 10A. Specifically, the air delivery conduit 730 includes a conduit portion 732 and a cover 734 that surrounds the conduit portion 732. As illustrated, the cover 734 has a web-like configuration. The materials for this cover may include silicone, rubbers and latex with a wall thickness from 0.2 mm to 1 mm, for example. The conduit portion itself may be made from thin silicone or polypropylene with a wall thickness from 0.2 mm to 1 mm, for example. However, other configurations are possible. When collapsed, the air delivery conduit 730 may be wrapped around the flow generator in a manner as described above. As shown in FIG. 10B, the conduit portion 732 may include built-in solid hoops 733 for extra support. FIG. 10B also illustrates air filled areas 735 within the conduit portion 732 when pressurized air is provided to the conduit portion 732. As shown in FIG. 10C, when the conduit portion 732 collapses, the solid hoops 733 are compressed and fold up in a concertina fold. This arrangement facilitates storage in a compact manner.

2.2.3 Air Delivery Conduit with Zipper

Figure 11A:
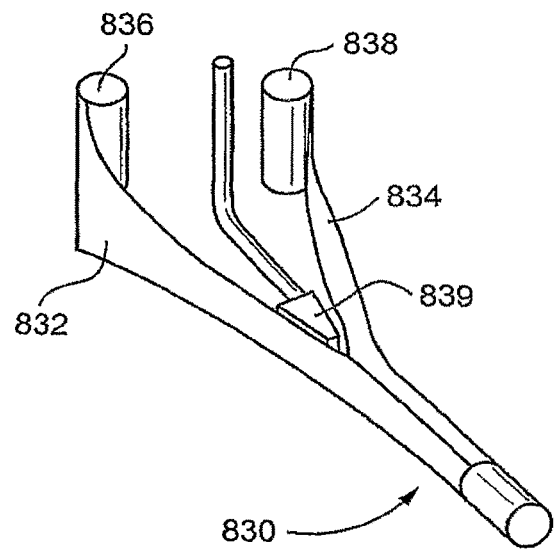
FIGS. 11A-11C illustrate an air delivery conduit according to another embodiment of the invention, the air delivery conduit adapted to be zip locked.

FIG. 11A illustrates an air delivery conduit 830 for a CPAP system that may be separated and stored in two sections 832, 834 that can be retracted within a storage space, e.g., provided by the flow generator. When the two sections 832, 834 are pulled out of the storage space, the two sections 832, 834 may be zipped together to form a sealed substantially rigid air delivery conduit 830 that allows the passage of air therethrough. Specifically, a first reel 836 is provided to dispense and retract a first section 832 of the air delivery conduit 830, and a second reel 838 is provided to dispense and retract a second section 834 of the air delivery conduit 830. The first and second sections 832, 834 are coupled by a zipper 839 that allows the first and second sections 832, 834 to be (1) separated for purposes of storing the first and second sections 832, 834 on respective reels 836, 838, and (2) coupled for purposes of establishing the air delivery conduit 830.

Figure 11B:
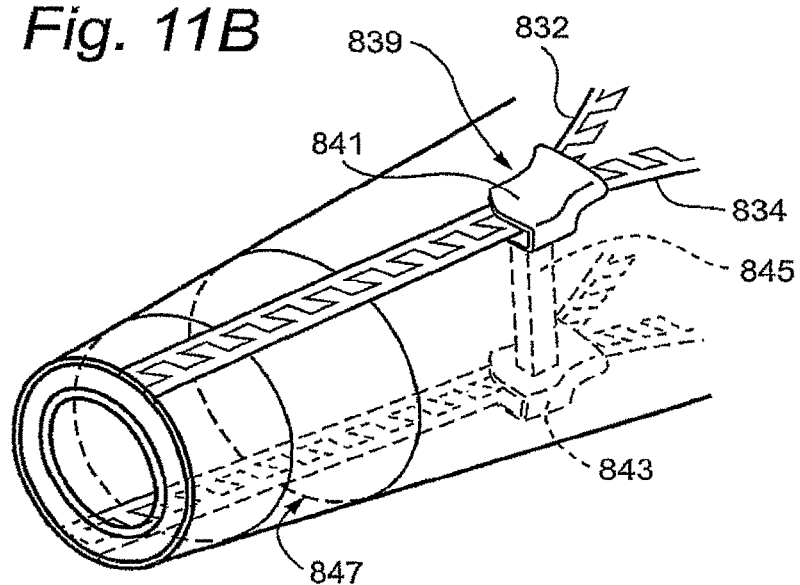
Figure 11C:
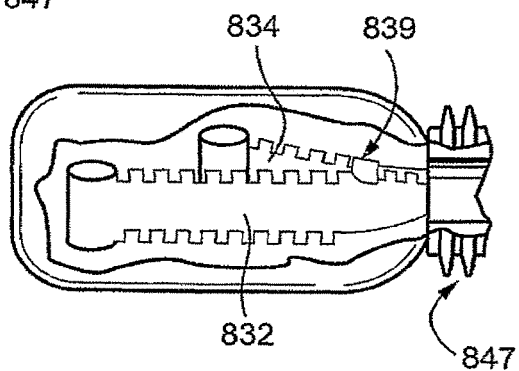

As shown in FIG. 11B, the zipper 839 includes two zipper slides 841, 843 and a connecting member 845 that couples the two zipper slides 841, 843. This zipper arrangement is used to provide support for the conduit 830 and a collapsible sealed collar 847 (see FIGS. 11B and 11C) used to seal air within the conduit 830. The zipper 839 may be constructed of polypropylene and the collapsible sealed collar 847 may be constructed of thin silicone or polypropylene (e.g., 1 mm to 0.2 mm thickness), for example. Tube connectors may be fixed to each end of the collapsible collar 847. In another embodiment, the air delivery conduit may include a single piece of material that may be stored in a substantially flat condition and then opposing sides of the material may be zipped together to establish a tube.

3. Air Delivery Conduit of CPAP System

In order to provide a more comfortable look and feel for the patient, an aspect of the present invention relates to an air delivery conduit between the flow generator and the patient interface with a reduced diameter, e.g., a diameter less than the typical 22 mm medical grade tubing. Preferably, the air delivery conduit (such as the air delivery conduits shown in FIGS. 6-9 and 9-11) has a diameter of about 15 mm although other diameters may be used. The reduced diameter will allow the air delivery conduit to be more flexible as the cross-sectional area is reduced and the stiffness of the conduit walls is reduced. The 15 mm conduit may be used to supply pressurized air greater than 15 $cmH_2O$. In an embodiment, the 15 mm conduit is used with a two-stage motor such as that described in ResMed's U.S. Pat. No. 6,910,483 to Daly et. al. This two-stage motor design may provide greater pressure rise and fall times.

Figure 12:
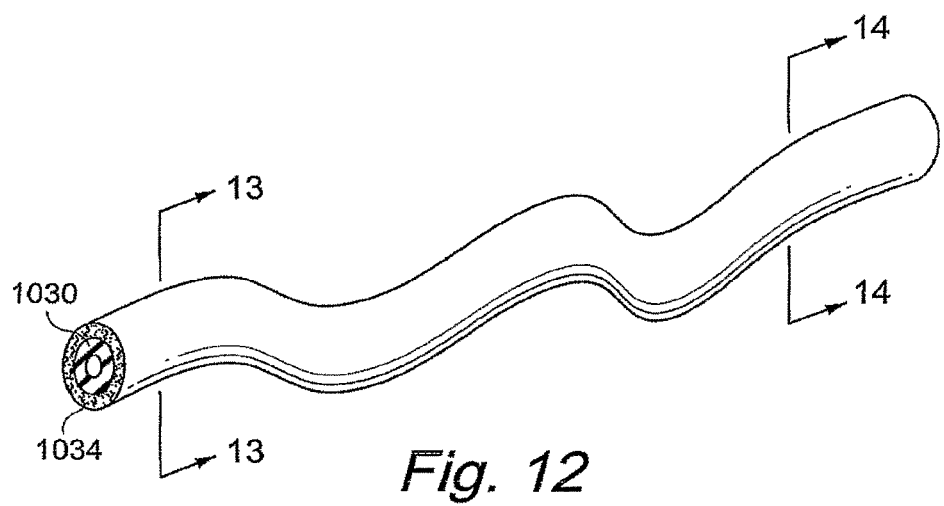
FIG. 12 is a perspective view of an air delivery conduit according to another embodiment of the invention.
Figure 13:
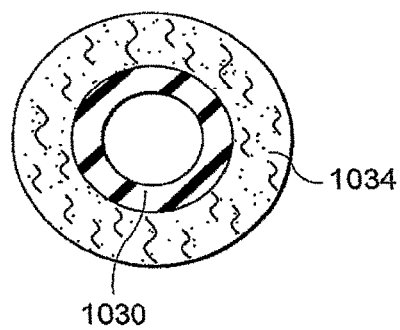
FIG. 13 is a cross-sectional view through line 13-13 of FIG. 12.
Figure 14:
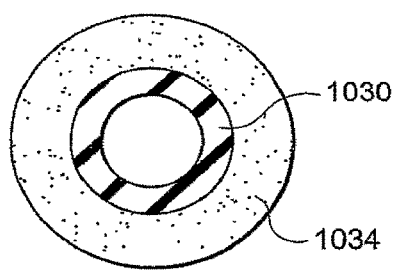
FIG. 14 is a cross-sectional view through line 14-14 of FIG. 12.

To enhance the aesthetic appeal of the air delivery conduit, a sock, sleeve or cover 1034 may be placed over the air delivery conduit 1030 as shown in FIG. 12. In an embodiment, the cover 1034 may have a silky external surface on at least the portion of the air delivery conduit 1030 that is closest to the patient as shown in FIG. 13. This arrangement may reduce the noise of the air delivery conduit 1030 as it brushes on material in and around the patient's bed. In another embodiment, the cover 1034 closest to the flow generator may be sticky or have larger coefficients of friction to restrict or limit movement of the air delivery conduit 1030 near the flow generator interface as shown in FIG. 14. Any suitable material may be used to cover the air delivery conduit 1030 including but not limited to cotton, nylon, polyester, or wool.

In another embodiment, the material used to cover the air delivery conduit may provide electrical communication for sensors near the patient interface back to the flow generator. The material may also provide heating or may be highly insulative to prevent or at least reduce "rainout". Further, the air delivery conduit may allow exhaust gases to be transmitted away from the patient through a helically wound section.

As a result of the above features, the air delivery conduit may be smaller, less intrusive, and more acceptable to the patient. In addition, the above features have the capability to increase the compliance of the air delivery conduit among patients.

3.1 Low Friction Air Delivery Conduit

Figure 16:
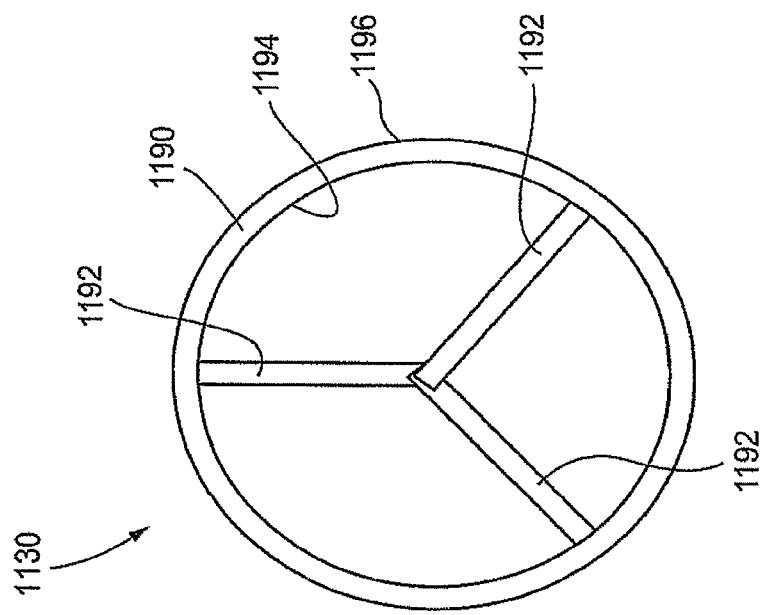
FIGS. 15-16 illustrate low friction air delivery conduits according to embodiments of the present invention.
Figure 15:
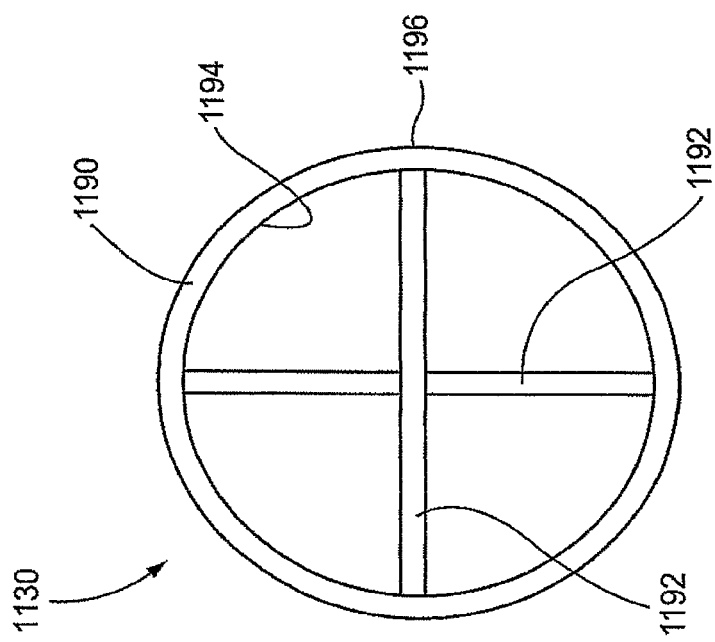

FIGS. 15-16 illustrate low friction air delivery conduits 1130 according to embodiments of the present invention. As illustrated, each air delivery conduit 1130 is in the form of a hose including a relatively thin tubular wall 1190, e.g., formed of extruded plastic, and at least one or more support webs 1192 that internally support the tubular wall 1190. The conduit 1130 may have any suitable length, which may depend on application.

The tubular wall 1190 is structured such that both internal and external surfaces 1194, 1196 of the tubular wall 1190 are very smooth, e.g., low friction surfaces. Exemplary materials of the tubular wall 1190 include polyethylene, polypropylene, polyolefins, silicones, and the like. Preferably, at least the external surface 1196 is smooth. The smooth external surface 1196 allows the conduit 1130 to slide across furniture and bed linen, for example, in a silent manner and with little resistance or friction. This provides more comfort to the patient, which may improve sleep quality and ease of use.

The support webs 1192 provide internal support to the tubular wall 1190. As illustrated, the webs 1192 extend across the internal diameter or a part thereof. Alternatively, the support web or webs 1192 may extend across a chord of the tubular wall 1190. In the illustrated embodiment, the support webs 1192 are equally spaced about the axis of the tubular wall 1190, and at least three webs 1192 are provided. For example, FIG. 15 illustrates webs 1192 arranged in a cruciform or cross shape, and FIG. 16 illustrates webs 1192 arranged in tri-lobial shape wherein the webs 1192 intersect at or about the axis of the tubular wall 1190. However, other web arrangements are possible. In an embodiment, the wall 1190 and webs 1192 may be co-extruded.

The support webs 1192 may be arranged in a helical fashion around the axis of the conduit 1130, along its length, to allow flexibility and increased crush resistance.

In an embodiment, the support webs 1192 may define two or more isolated passages through the conduit 1130. The passages may be used for air delivery, venting, electrical wiring, pressure measurement, etc.

Furthermore, there is no requirement that the conduit has to be round using this system. For example, any cross-sectional shape that does not include sharp corners may be used, e.g., an oval cross-section.

The low friction air delivery conduit is also disclosed in PCT Application No. PCT/AU2006/000679, which is incorporated herein by reference in its entirety.

4. Connectors for CPAP System

Another aspect of the present invention relates to a CPAP system that includes a flow generator connector for use in coupling one end of the air delivery conduit to the flow generator, and a patient interface connector for use in coupling the other end of the air delivery conduit to the patient interface.

4.1 Connectors with Recognition System

To use an air delivery conduit with a smaller diameter, e.g., 15 mm, the pressure output requirements of the flow generator should be capable of responding quickly to provide sufficient pressure outputs. Thus, the performance of the flow generator is very important in providing adequate CPAP therapy. Therefore, the flow generator should know when a smaller diameter air delivery conduit is being used to enable correct performance.

Consequently, one aspect of the present invention relates to a recognition system for the CPAP system that is structured to signal the flow generator the type (e.g., size, length, etc.) of air delivery conduit being attached. This allows the flow generator to recognize or identify the air delivery conduit selected by the patient so that appropriate operating parameters of the flow generator may be selected, e.g., automatically selected, to coordinate with the selected air delivery conduit. Thus, the flow generator can operate more efficiently as the flow generator can select operating parameters that are specifically optimized for the selected air delivery conduit.

In an embodiment, the recognition system may include magnetic reed switches, hall effect sensors, inductive loop detectors, or the like within the flow generator connector and the flow generator that allow recognition of the air delivery conduit by the flow generator. This arrangement ensures correct performance of the flow generator for the specific air delivery conduit being used.

Figure 17A:
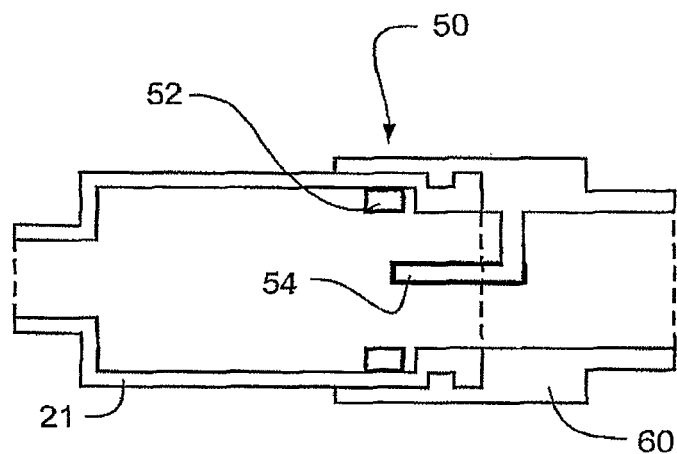
FIGS. 17A and 17B are diagrams illustrating a recognition system including magnetic reed switches according to embodiments of the invention.
Figure 17B:
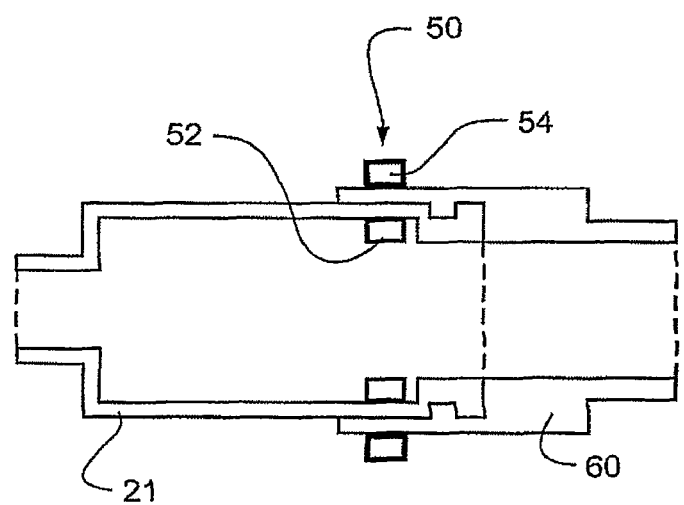

For example, FIGS. 17A and 17B illustrate a recognition system 50 according to an embodiment of the present invention. As illustrated, the outlet 21 of the flow generator includes a reed switch 52, and the flow generator connector 60 (which interconnects the air delivery conduit and the outlet 21 of the flow generator) includes a magnet 54. The reed switch 52 may be annular shaped and provided on an interior surface of the outlet 21 of the flow generator (see FIGS. 17A and 17B). The magnet 54 may be provided as a magnetic rod that extends along an interior of the flow generator connector 60 (see FIG. 17A), or the Magnet 54 may be annular shaped and provided on an exterior surface of the flow generator connector 60 (see FIG. 17B). When the flow generator connector 60 is engaged with the outlet 21 of the flow generator (as shown in FIGS. 17A and 17B), the magnet 54 of the flow generator connector 60 provides a signal to the reed switch 52 of the outlet 21 so that the flow generator can recognize or identify the selected air delivery conduit associated with the flow generator connector 60.

It should be understood that the flow generator connector 60 may have any suitable configuration, e.g., straight tube, right-handed elbow, etc, and may be coupled to the outlet 21 in any suitable manner, e.g., snap-fit. Also, the flow generator connector and the patient interface connector on opposing sides of the air delivery conduit may be interchangeable and may both include a magnet 54 to signal the reed switch 52 within the outlet 21 of the flow generator.

4.2 Snap-Fit Connectors

FIGS. 18-23 illustrate a CPAP system 900 according to yet another embodiment of the present invention that includes quick, snap-fit connectors 960, 970 to facilitate attachment of the air delivery conduit 930 between the flow generator 920 and the patient interface 940. The snap-fit connectors 960, 970 are less bulky than known rubber cuffs and are ergonomically easier to handle and attach/detach. The snap-fit connection also provides an audible indication that a proper connection has been established.

Specifically, as shown in FIGS. 18 and 19, the CPAP system 900 includes a flow generator 920 with an outlet 921, a patient interface 940, e.g., nasal assembly, an air delivery conduit 930, a snap-fit patient interface connector 970 that couples one end of the air delivery conduit 930 to the patient interface 940, and a snap-fit flow generator connector 960 that couples the other end of the air delivery conduit 930 to the outlet 921 of the flow generator 920.

Figure 21:
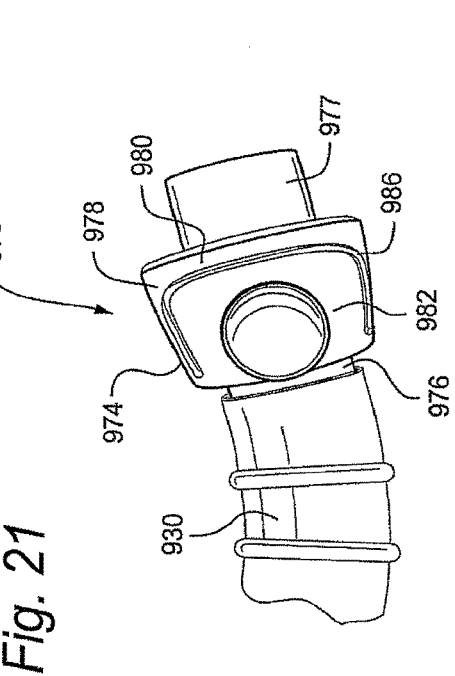
FIG. 21 is a perspective view of a second portion of a patient interface connector of the CPAP system shown in FIG. 18.
Figure 20:
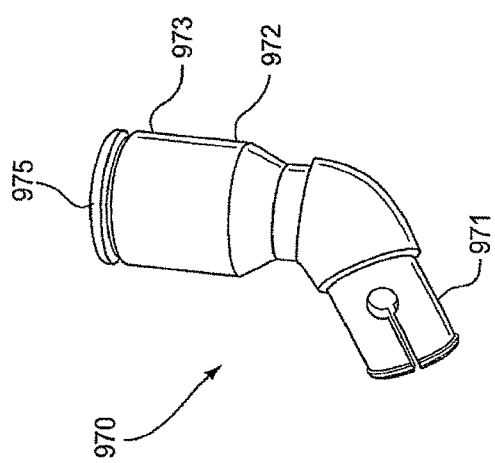
FIG. 20 is a perspective view of a first portion of a patient interface connector of the CPAP system shown in FIG. 18.
Figure 23:
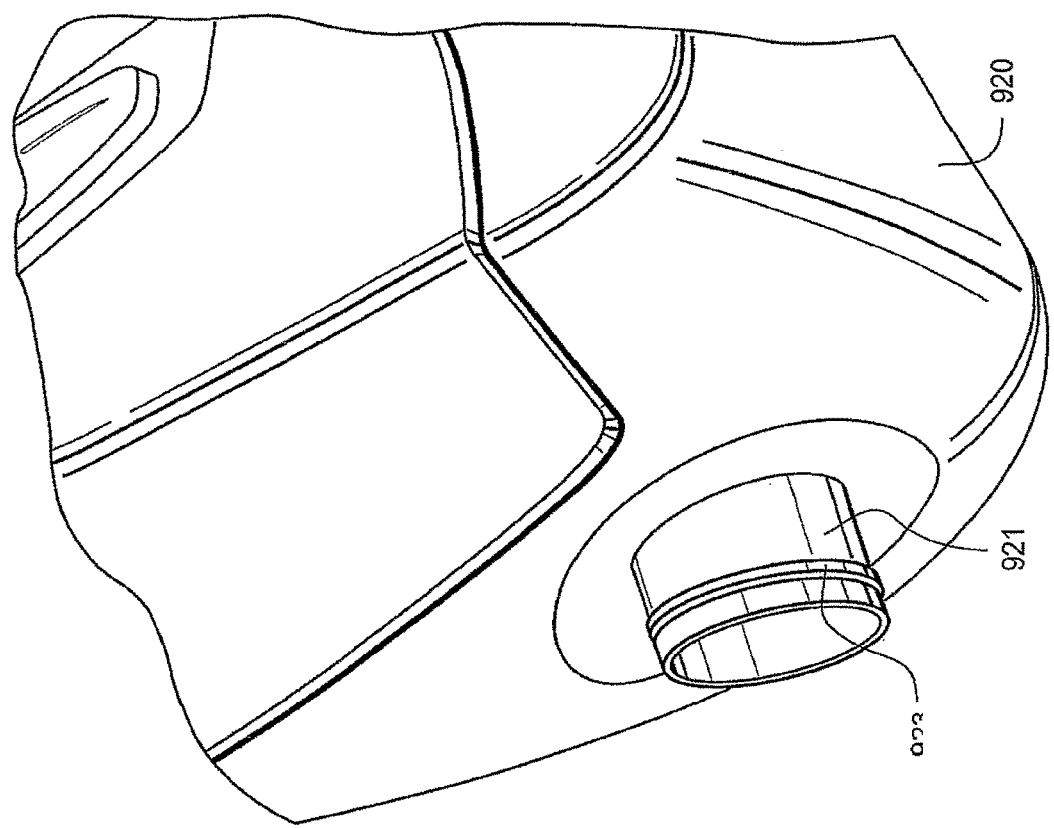
FIG. 23 is an enlarged isolated perspective view of a flow generator of the CPAP system shown in FIG. 18.

The patient interface connector 970 includes first and second portions 972, 974 that are releasably engagable with one another with a snap-fit. As best shown in FIG. 20, the first portion 972 has an elbow-like configuration with one conduit end 971 adapted to be coupled to the patient interface 940, e.g., split barb arrangement, and an opposite conduit end 973 that provides an annular flange 975. As best shown in FIG. 21, the second portion 974 has one conduit end 976 adapted to be coupled to the air delivery conduit 930, e.g., friction fit, and an opposite conduit end that provides a conduit section 977 adapted to engage within the conduit end 973 of the first portion 972 and a flexible quick release mechanism 978 adapted to engage the flange 975 of the first portion 972.

The flexible quick release mechanism 978 includes a collar 980 that surrounds the conduit section 977 and an apron 982. The collar 980 includes opposing T-shaped members 984 (see FIG. 18) and the apron 982 is connected to a lower leg of each of the T-shaped members 984. The collar 980 is spaced away from the conduit section 977 so as to form a receiving space therebetween. Two grooves 986 are provided between the collar 980 and the apron 982 that allow the collar 980 to flex.

The first portion 972 is coupled with the second portion 974 by inserting the flange 975 into the receiving space between the collar 980 and the conduit section 977 until it engages protrusions (not shown), e.g., two protrusions, formed on the inside surface of the collar 980. The protrusions are structured such that engagement with the flange 975 causes outward flexure of the collar 980 until the flange 975 is received with the grooves 986. The collar 980 then returns to its unflexed state to secure the first portion 972 to the second portion 974. The engagement between the collar 980 and the flange 975 during the snap-action connection of the first and second portions 972, 974 may result in an audible click to signal a secure connection. Also, the connection may allow the first and second portions 972, 974 to freely rotate or swivel with respect to one another. To release the first and second portions 972, 974, opposing sides of the collar 980 are flexed towards one another to allow passage of the flange 975 from the protrusions. Further details of such a snap-fit connection are provided in U.S. patent application Ser. No. 10/390,720, filed Mar. 19, 2003 (published as U.S. Patent Publication No. 2003-0196662), the entirety incorporated herein by reference.

Figure 22:
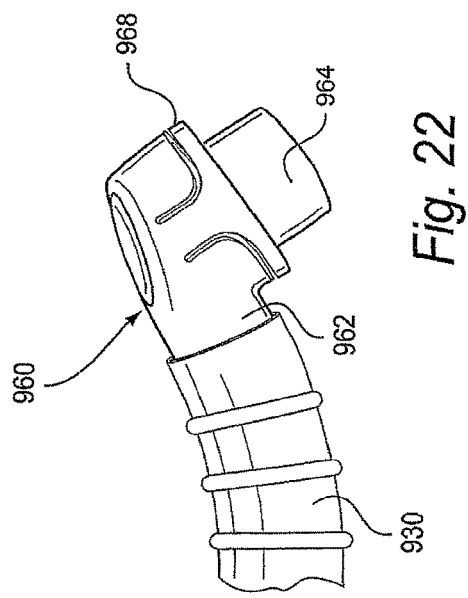
FIG. 22 is a perspective view of a flow generator connector of the CPAP system shown in FIG. 18.

As best shown in FIG. 22, the flow generator connector 960 has an elbow-like configuration with one conduit end 962 adapted to be coupled to the air delivery conduit 930, e.g., friction fit, and an opposite conduit end that provides a conduit section 964 adapted to engage within the outlet 921 of the flow generator 920 and a flexible quick release mechanism 968 adapted to engage a flange 923 (see FIG. 23) provided on the outlet 921 of the flow generator 920. The flexible quick release mechanism 968 of the flow generator connector 960 is substantially similar to the mechanism 978 of the patient interface connector 970, and is releasably coupled to the outlet flange 923 of the flow generator 920 in a similar manner as described above.

The connectors 960, 970 may be molded from any suitable material, e.g., polypropylene or polycarbonate.

The snap-fit connectors 960, 970 allow for rapid and precise connection between the air delivery conduit 930 and the patient interface 940 and/or between the air delivery conduit 930 and the flow generator 920. It also allows for simple disassembly, e.g., for cleaning, transport, and storage.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. In addition, while the invention has particular application to patients who suffer from OSA, it is to be appreciated that patients who suffer from other illnesses (e.g., congestive heart failure, diabetes, morbid obesity, stroke, barriatric surgery, etc.) can derive benefit from the above teachings. Moreover, the above teachings have applicability with patients and non-patients alike in non-medical applications.

What is claimed is:

1. A continuous positive airway pressure (CPAP) system for treating sleep disordered breathing in a patient, the system comprising:
   a flow generator providing an outlet and configured to deliver breathable gas to the patient at a pressure of between 3cmH$_2$O to 20cmH$_2$O through the outlet and to at least one airway of the patient to act as at least a partial splint on the at least one airway while the patient is sleeping;
   a patient interface configured to engage the face of the patient and provide a seal over the at least one airway of the patient,
   an air delivery conduit that is configured to deliver the breathable gas provided by the flow generator to the patient interface and the at least one airway of the patient; and
   at least one connector that is configured to couple the air delivery conduit to at least one CPAP component that includes at least one of the patient interface and the outlet of the flow generator, wherein the at least one connector includes first and second portions, wherein the first portion includes a flange configured to engage with at least one protrusion of the second portion that causes the flange to be received into at least one groove of the second portion, wherein the first portion is configured to engage one of the air delivery conduit and the CPAP component and the second portion is configured to engage the other of the air delivery conduit and the CPAP component, wherein connection between the first and second portions of the at least one connector thereby forms an airflow path that includes at least the CPAP component and the air delivery conduit, where fitting the flange of the first portion to the second portion provides a specific audible indication when properly coupled.

2. The CPAP system of claim 1, further comprising a recognition system structured to recognize or identify a specific type of the CPAP component that is connected to the CPAP system.

3. The CPAP system of claim 2, wherein the flow generator is further configured to automatically select or adjust operating parameters related to the delivery of breathable gas based on the recognition or identification of the corresponding specific type of CPAP component.

4. The CPAP system of claim 1, wherein the at least one connector includes at least one structural identification element configured to signal the flow generator to thereby uniquely recognize or identify a specific type of the CPAP component.

5. The CPAP system of claim 1, wherein the at least one connector includes a quick-release component that allows for uncoupling of the at least one CPAP component.

6. A continuous positive airway pressure (CPAP) system for treating sleep disordered breathing in a patient, the system comprising:
   a flow generator providing an outlet and configured to deliver breathable gas to the patient at a pressure of between 3cmH$_2$O to 20cmH$_2$O through the outlet and to at least one airway of the patient to act as at least a partial splint on the at least one airway while the patient is sleeping;
   an air delivery conduit configured to couple to the outlet of the flow generator;
   a patient interface configured to engage the face of the patient and provide a seal over the at least one airway of the patient, the patient interface configured to couple to another end of the air delivery conduit to thereby provide an airflow path from the outlet of the flow generator to the at least one airway of the patient to which the breathable gas is delivered, the airflow path including the patient interface and the air delivery conduit; and at least one structural identification element disposed in correspondence with the air delivery conduit, the at least one structural identification element configured to signal the flow generator to thereby uniquely recognize or identify a corresponding type of CPAP component that is part of the airflow path.

7. The CPAP system of claim 6, wherein the at least one structural identification element includes a magnet.

8. The CPAP system of claim 7, further comprising: a recognition system structured to recognize or identify the corresponding type of CPAP component and communicate with the flow generator to control the delivery of the breathable gas.

9. The CPAP system of claim 6, wherein the structural identification element is configured to wirelessly signal a recognition system of the flow generator to thereby enable recognition or identification of the corresponding type of CPAP component.

10. The CPAP system of claim 6, wherein the flow generator is further configured to automatically select and/or adjust operating parameters related to the delivery of breathable gas based on the recognition or identification of the corresponding type of CPAP component.

11. The CPAP system of claim 6, further comprising a connector configured to couple the air delivery conduit to the flow generator or the air delivery conduit to the patient interface, the connector including the at least one structural identification element.

12. The CPAP system of claim 11, wherein the connector is a snap-fit connector that provides a corresponding audible indication when the snap-fit connector is properly fitted or connected to the flow generator or patient interface.

13. The CPAP system of claim 11, wherein the at least one connector includes first and second portions, wherein the first portion includes a flange configured to engage with at least one protrusion of the second portion that causes the flange to be received into at least one groove of the second portion, wherein the first portion is configured to engage one of the air delivery conduit and the patient interface or the outlet and the second portion is configured to engage the other of the air delivery conduit and the patient interface or the outlet, wherein connection between the first and second portions is included in the airflow path between the outlet and the at least one airway of the patient.

14. The CPAP system of claim 13, wherein fitting the flange of the first portion to the second portion provides an audible indication when properly coupled.

15. The CPAP system of claim 6, wherein the air delivery conduit includes a connector that is configured to physically couple the air delivery conduit to the outlet or the patient interface.

16. The CPAP system of claim 15, wherein the connector includes the at least one structural identification element that is a magnet.

17. The CPAP system of claim 16, wherein the magnet is disposed on the exterior of the connector.

18. The CPAP system of claim 16, wherein the magnet is disposed on the interior of the connector.

19. The CPAP system of claim 6, wherein the flow generator operates with increased efficiency as a result of the unique recognition or identification of the corresponding type of CPAP component.

* * * * *